United States Patent
Shi et al.

(10) Patent No.: US 12,090,245 B2
(45) Date of Patent: Sep. 17, 2024

(54) TISSUE ADHESIVE MEMBRANE AND PREPARATION METHOD THEREOF

(71) Applicant: SOUTH CHINA UNIVERSITY OF TECHNOLOGY, Guangzhou (CN)

(72) Inventors: Xuetao Shi, Guangzhou (CN); Wei Yang, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 18/144,859

(22) Filed: May 9, 2023

(65) Prior Publication Data

US 2023/0414827 A1    Dec. 28, 2023

(30) Foreign Application Priority Data

Jun. 23, 2022 (CN) .......................... 202210716470.2

(51) Int. Cl.
| | |
|---|---|
| A61L 24/06 | (2006.01) |
| C08G 83/00 | (2006.01) |
| C08L 29/04 | (2006.01) |
| A61L 24/00 | (2006.01) |

(52) U.S. Cl.
CPC ............ *A61L 24/06* (2013.01); *C08G 83/008* (2013.01); *C08L 29/04* (2013.01); *A61L 24/0015* (2013.01); *C08G 2170/00* (2013.01); *C08L 2203/02* (2013.01); *C08L 2203/162* (2013.01)

(58) Field of Classification Search
None
See application file for complete search history.

(56) References Cited

U.S. PATENT DOCUMENTS

| | | | | |
|---|---|---|---|---|
| 4,386,183 A | * | 5/1983 | Wempe ................ | C09D 129/04 524/405 |
| 4,694,103 A | * | 9/1987 | Krepski ................ | A61K 6/887 546/330 |
| 8,790,632 B2 | * | 7/2014 | Arthur ................ | A61L 24/043 424/78.17 |

FOREIGN PATENT DOCUMENTS

WO    WO 2018/197706    * 11/2018

OTHER PUBLICATIONS

Zhang et al., (Sci. Adv. 2018; 4 : eaat8192, 1-8) Exploring a naturally tailored small molecule for stretchable, self-healin ive supramolecular polymers.*
Chen et al. (Biomater. Sci., 2020, 8, 6235-6245) Supramolecular medical antibacterial tissue adhesive prepared based on natural small molecules.*
ASTM Designation: F2258-05, Standard Test Method for Strength Properties of Tissue Adhesives in Tension, ASTM International, 2015, pp. 1-5.
ASTM Designation: F2392-04, Standard Test Method for Burst Strength of Surgical Sealants, ASTM International, 2015.

* cited by examiner

*Primary Examiner* — Tigabu Kassa
(74) *Attorney, Agent, or Firm* — Bayramoglu Law Offices LLC

(57) ABSTRACT

A tissue adhesive membrane and a preparation method thereof are provided. The tissue adhesive membrane includes a supramolecular polymer and an enhancer; the supramolecular polymer is prepared by copolymerization of lipoic acid and a biocompatible stabilizer; and the enhancer includes at least one selected from the group consisting of a cationic compound, a cationic polymer, and a metal particle. The tissue adhesive membrane of the present invention can achieve rapid adhesion, seal wounds continuously and effectively, and maintain long-lasting mechanical strength. The components of the tissue adhesive membrane come from natural components of animals and plants, have good biocompatibility, and possess the functions of antibacterial and inhibiting inflammation. The tissue adhesive membrane of the present invention is a hydrophobic adhesive membrane where hydrogen bonding and high surface energy can provide strong adhesion energy and no adverse active groups that may cause irritation or discomfort are contained.

6 Claims, 1 Drawing Sheet

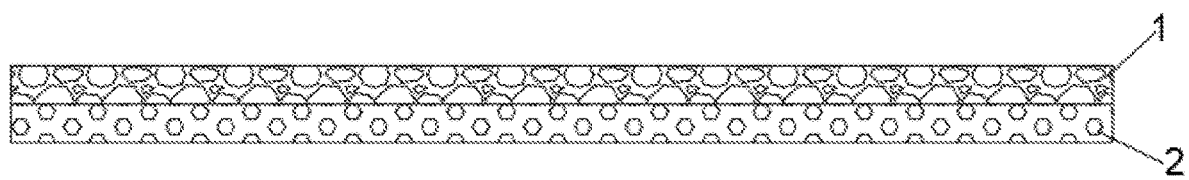

TISSUE ADHESIVE MEMBRANE AND PREPARATION METHOD THEREOF

CROSS REFERENCE TO RELATED APPLICATIONS

This application is based upon and claims priority to Chinese Patent Application No. 202210716470.2, filed on Jun. 23, 2022, the entire contents of which are incorporated herein by reference.

TECHNICAL FIELD

The present invention relates to the technical field of medical membranes, in particular to a tissue adhesive membrane and a preparation method thereof.

BACKGROUND

The closure of wounded tissue is an inevitable clinical process. Traditional suture surgery causes secondary damage to the tissue and requires a long operation time, which is prone to risk of infection. Tissue adhesive membrane has gradually received attention because of its convenient operation, high efficiency of wound closure, and avoidance of secondary injury due to less material intervention. It can replace sutures for some surgical wound closures. However, as a medical implant tissue adhesive patch, higher requirements are put forward for its biocompatibility, continuous adhesion, and mechanical strength.

Liquid adhesives and adhesive patches have a similar function to tissue adhesive membranes in the prior art. The liquid adhesives can realize wound closure of the tissue after curing, but they are easy to be diluted by tissue blood during the curing process, resulting in unstable adhesion and entry of a large amount of adhesives into blood circulation system. The adhesive patches rapidly seal wounds, but most of them function based on unreacted active groups chemically reacting with the tissue surface, which is accompanied by local high heat and leads to inflammation. Simultaneously, excessive degradation products and foreign toxic components increase the burden on the liver and kidneys. Tissue adhesive membranes are a comprehensive and more effective means of wound closure. However, most of the bioadhesive membranes currently studied can only be applied to the skin surface, and it is difficult to maintain the continuous adhesion and mechanical strength of the membranes in internal liquid environment, which undoubtedly limits the further development of tissue adhesive membranes.

SUMMARY

The first objective of the present invention is to overcome the shortcomings and deficiencies of the prior art and to provide a tissue adhesive membrane that can realize rapid adhesion with wet tissue, stable mechanical properties, and biodegradability.

The second objective of the present invention is to provide a preparation method for the tissue adhesive membrane.

The first objective of the present invention is realized by the following technical solution: A tissue adhesive membrane, including a functional layer formed by a supramolecular polymer and an enhancer; the supramolecular polymer is prepared by copolymerization of lipoic acid and a biocompatible stabilizer; the enhancer includes at least one selected from the group consisting of a cationic compound, a cationic polymer, and a metal particle.

Further, the tissue adhesive membrane also includes a sacrificial layer, and the sacrificial layer is provided on either side or both sides of the functional layer.

Further, the supramolecular polymer is at least one selected from the group consisting of a multi-carboxyl polymer, a benzene polyphenol derivative, a multi-cyanide polymer, and an activated ester polymer.

Further, the stabilizer includes at least one selected from the group consisting of an acrylate derivative, a sulfhydryl derivative, and the benzene polyphenol derivative.

Further, the acrylate derivative is N-acryloyloxy glycine.

Further, the cationic compound is at least one selected from the group consisting of zinc sulfate, magnesium sulfate, copper sulfate, silver nitrate, ferric chloride, and ferrous chloride.

Further, the metal particle is at least one selected from the group consisting of ferroferric oxide, ferric oxide, zinc oxide, and iron.

Further, a thickness of the tissue adhesive membrane is not more than 2 mm.

Further, the sacrificial layer is polyvinyl alcohol (PVA).

The second objective of the present invention is realized by the following technical solution: A preparation method of the tissue adhesive membrane, including the following steps:

preparing a mixed solution of the lipoic acid, the stabilizer, and the enhancer in ethanol, performing a thermal-initiated polymerization to obtain a supramolecular polymer solution A;

uniformly adding the A to a silicon wafer by spin coating for 10-200 s using a spin coating instrument, drying to obtain an adhesive membrane B; and adding a PVA aqueous solution to the B by spin coating for 10-200 s using the spin coating instrument to form the sacrificial layer, drying to obtain the tissue adhesive membrane.

Further, a molar ratio of the lipoic acid, the stabilizer, and the enhancer is 1:(0.5-1):(0.001-0.01).

Further, a mass fraction of the lipoic acid is 40%-80%.

Further, the thermal-initiated polymerization is performed at 50-100° C.

Further, a mass fraction of the PVA aqueous solution is 5%-30%.

Further, the spin coating is conducted at a speed of 500-5000 rpm and an acceleration of 50-1000 rpm.

Compared with the prior art, the present invention has the following advantages:

1. The tissue adhesive membrane of the present invention can achieve rapid adhesion, seal wounds continuously and effectively, and maintain long-lasting mechanical strength.

2. The components of the tissue adhesive membrane of the present invention come from natural components of animals and plants, have good biocompatibility, and possess the functions of antibacterial and inhibiting inflammation.

3. The tissue adhesive membrane of the present invention is a hydrophobic adhesive membrane where hydrogen bonding and high surface energy can provide strong adhesion energy and no adverse active groups that may cause irritation or discomfort are contained.

BRIEF DESCRIPTION OF THE DRAWING

FIGURE shows a cross-sectional view of the tissue adhesive membrane provided in the embodiment.

DETAILED DESCRIPTION OF THE EMBODIMENTS

The present invention is further described in detail below, but the embodiments of the present invention are not limited herein.

As shown in the figure, the present invention provides a tissue adhesive membrane, including the functional layer 1 and the sacrificial layer 2. The sacrificial layer 2 is provided on either side of the functional layer 1, or the sacrificial layer 2 is provided on both sides of the functional layer 1. The functional layer 1 includes a supramolecular polymer and an enhancer. The supramolecular polymer is prepared by copolymerization of lipoic acid and a biocompatible stabilizer. The enhancer includes at least one selected from the group consisting of a cationic compound, a cationic polymer, and a metal particle. The sacrificial layer 2 is a water-soluble polymer which can thicken the whole adhesive membrane after binding with the functional layer 1. As a result, it is conducive to tearing and removing from a mold. Moreover, the membrane has improved stability in the air and is not easily curled. After adhered to the tissue, the sacrificial layer can be quickly dissolved under the action of salt water to reduce the thickness of the membrane, improve the surface energy, and increase the adhesion between the membrane and the tissue.

In the embodiment, the supramolecular polymer is at least one selected from the group consisting of a multi-carboxyl polymer, a benzene polyphenol derivative, a multi-cyanide polymer, and an activated ester polymer.

In the embodiment, the stabilizer includes at least one selected from the group consisting of an acrylate derivative, a sulfhydryl derivative, and the benzene polyphenol derivative.

In the embodiment, the stabilizer is N-acryloyloxy glycine.

In the embodiment, the cationic compound is at least one selected from the group consisting of zinc sulfate, magnesium sulfate, copper sulfate, silver nitrate, ferric chloride, and ferrous chloride. Further, the metal particle can be subjected to complexation with the multi-carboxyl derivative to improve the mechanical strength of the supramolecular polymer and improve the mechanical stability. Further, the metal particle can also be subjected to complexation with the tissue surface to enhance the adhesion. Further, the complexing network can be removed under the action of the external reagent ethylenediaminetetraacetic acid (EDTA) to achieve tissue adhesion and de-adhesion as needed.

In the embodiment, the metal particle is at least one selected from the group consisting of ferroferric oxide, ferric oxide, zinc oxide, and iron.

In the embodiment, a thickness of the tissue adhesive membrane is not more than 2 mm. The thickness decreases, the specific surface area increases, the surface energy increases, the hydrogen bonding between the adhesive membrane and tissue increases, and the adhesion increases.

In the embodiment, the sacrificial layer is PVA.

A preparation method for the tissue adhesive membrane is further provided in the present invention, including the following steps:

A mixed solution of the lipoic acid, the stabilizer, and the enhancer is prepared in ethanol, and a thermal-initiated polymerization is performed to obtain a supramolecular polymer solution A.

The A is uniformly added to a silicon wafer by spin coating for 10-200 s using a spin coating instrument, followed by drying to obtain an adhesive membrane B.

A PVA aqueous solution is added to the B by spin coating for 10-200 s using the spin coating instrument to form the sacrificial layer, Followed by drying to obtain the tissue adhesive membrane.

In the embodiment, a molar ratio of the lipoic acid, the stabilizer, and the enhancer is 1:(0.5-1):(0.001-0.01).

In the embodiment, a mass fraction of the lipoic acid is 40%-80%.

In the embodiment, the thermal-initiated polymerization is performed at 50-100° C.

In the embodiment, a mass fraction of the PVA aqueous solution is 5%-30%.

In the embodiment, the spin coating is conducted at a speed of 500-5000 rpm and an acceleration of 50-1000 rpm.

The tissue adhesive membrane of the present invention is described in more detail below in combination with several embodiments and comparative examples.

Embodiment 1

1) A lipoic acid-ethanol solution with a mass fraction of lipoic acid being 60% is prepared, and then N-acryloyloxy glycine and zinc sulfate are added therein. The molar ratio of the lipoic acid, the N-acryloyloxy glycine, and the zinc sulfate is 1:0.5:0.01. A thermal-initiated polymerization is performed at 75° C. to yield a supramolecular polymer solution A.

2) The A is uniformly added to a silicon wafer by spin coating for 30 s using a spin coating instrument (3000 rpm), followed by drying to obtain an adhesive membrane B.

3) A PVA aqueous solution with a mass fraction of 20% is added to the B by spin coating for 30 s using the spin coating instrument (3000 rpm) to form the sacrificial layer, followed by drying to obtain the tissue adhesive membrane.

Embodiment 2

Different from Embodiment 1, the mass fraction of lipoic acid in step 1) is 40%.

Embodiment 3

Different from Embodiment 1, the molar ratio of the lipoic acid, the N-acryloyloxy glycine, and the zinc sulfate in step 1) is 1:0.5:0.001.

Embodiment 4

Different from Embodiment 1, the molar ratio of the lipoic acid, the N-acryloyloxy glycine, and the zinc sulfate in step 1) is 1:0.5:0.005.

Embodiment 5

Different from Embodiment 1, the molar ratio of the lipoic acid, the N-acryloyloxy glycine, and the zinc sulfate in Step 1) is 1:0.2:0.01.

Embodiment 6

Different from Embodiment 1, the molar ratio of the lipoic acid, the N-acryloyloxy glycine, and the zinc sulfate in step 1) is 1:1:0.01.

Embodiment 7

Different from Embodiment 1, the thermal-initiated polymerization in step 1) is performed at 50° C.

Embodiment 8

Different from Embodiment 1, the speed of the spin coating in step 2) and step 3) is 800 rpm.

Embodiment 9

Different from Embodiment 1, the mass fraction of the PVA aqueous solution in step 3) is 15%.

Comparative Example 1

Different from Embodiment 1, there is no sacrificial layer in step 3).

Comparative Example 2

Different from Embodiment 1, the mass fraction of lipoic acid in step 1) is 20%.

Comparative Example 3

Different from Embodiment 1, there is no stabilizer N-acryloyloxy glycine in step 1).

Comparative Example 4

Different from Embodiment 1, there is no enhancer zinc sulfate in step 1).

Test and Evaluation

Different indexes of the products obtained by the above embodiments and comparative examples are tested. The adhesive properties are tested by ASTM F 2258-05 "Standard Test Method for Strength Properties of Tissue Adhesives in Lap-Shear by Tension Loading". The bursting pressure is tested by ASTM Method F 2392-04 "Standard Test Method for Burst Strength of Surgical Sealants". Meanwhile, the elastic modulus and underwater swelling performance of the samples are tested. All samples are kept under the same conditions and environment for the same test. The test results are shown in Table 1.

TABLE 1

| Samples to be tested | Adhesive strength (N) | Bursting pressure (mmHg) | Elastic modulus (MPa) | Swelling rate (%) |
|---|---|---|---|---|
| Embodiment 1 | 5.32 | 126 | 0.82 | 106 |
| Embodiment 2 | 4.16 | 98 | 0.60 | 113 |
| Embodiment 3 | 4.62 | 106 | 0.62 | 137 |
| Embodiment 4 | 5.05 | 117 | 0.73 | 123 |
| Embodiment 5 | 4.76 | 82 | 0.58 | 103 |
| Embodiment 6 | 4.26 | 103 | 0.79 | 128 |
| Embodiment 7 | 4.76 | 108 | 0.53 | 136 |
| Embodiment 8 | 5.87 | 137 | 0.85 | 104 |
| Embodiment 9 | 5.16 | 103 | 0.67 | 108 |
| Comparative example 1 | 1.26 | 46 | 0.32 | 105 |
| Comparative example 2 | 1.38 | 53 | 0.37 | 157 |
| Comparative example 3 | 1.86 | 56 | 0.28 | 103 |
| Comparative example 4 | 2.34 | 39 | 0.47 | 112 |

Embodiment 1, 2, and comparative example 2 in Table 1 show that the proportion of lipoic acid affects the supramolecular structure, and thus significantly changes the adhesive properties and elastic modulus. The Comparison between Embodiments 3-6 and comparative examples 3-4 shows that the stabilizer and the enhancer have a significant influence on the adhesive strength and the mechanical strength of the supramolecular polymer, the stabilizer terminates the unstable process of the sulfhydryl group of lipoic acid and significantly regulates the molecular weight of the supramolecular polymer, while the enhancer has an obvious complexation effect on acid and changes the cross-linking density between molecules. Meanwhile, the enhancer zinc ion complexes with the acid groups on the tissue surface and changes the adhesive strength. Embodiment 7 shows that changing the thermal-initiated polymerization temperature affects the polymerization degree of lipoic acid and has a regulating effect on the overall performance. Embodiments 9 and comparative example 1 demonstrate that the sacrificial layer enhances the mechanical strength of the membrane and facilitates overall application such as removal from a mold and auxiliary bonding.

The above embodiments are preferred embodiments of the present invention, but the embodiments of the present invention are not limited by the above embodiments. Any other changes, modifications, substitutions, combinations, and simplifications that do not deviate from the spirit essence and principle of the present invention shall be equivalent replacements and shall be covered by the scope of protection of the present invention.

What is claimed is:

1. A tissue adhesive membrane, comprising:
   a functional layer formed by a supramolecular polymer and an enhancer, and a sacrificial layer provided on either side or both sides of the functional layer; wherein
   the sacrificial layer is polyvinyl alcohol (PVA), and the sacrificial layer is dissolvable under the action of salt water after the tissue adhesive membrane is adhered to the tissue;
   the supramolecular polymer is prepared by a copolymerization of lipoic acid and a biocompatible stabilizer;
   the biocompatible stabilizer is N-acryloyloxy glycine;
   the enhancer is zinc sulfate;
   a molar ratio of the lipoic acid, the biocompatible stabilizer, and the enhancer is 1:(0.5-1):(0.001-0.01); and
   a mass fraction of the lipoic acid in a solvent is 40%-80%.

2. The tissue adhesive membrane according to claim 1, wherein a thickness of the tissue adhesive membrane is not more than 2 mm.

3. The tissue adhesive membrane according to claim 1, wherein the supramolecular polymer product comprises an adhesive strength of 4.16-5.32 N, a bursting pressure of 98-126 mmHg, an elastic modulus of 0.60-0.82 MPa, and a swelling rate of 106-137%.

4. A preparation method for the tissue adhesive membrane according to claim 1, comprising the following steps:
   preparing a mixed solution of the lipoic acid, the biocompatible stabilizer, and the enhancer in ethanol, performing a thermal-initiated polymerization to obtain a supramolecular polymer solution;
   uniformly adding the supramolecular polymer solution to a silicon wafer by spin coating for 10-200 s using a spin coating instrument, drying to obtain an adhesive membrane; and
   adding a PVA aqueous solution to the adhesive membrane by spin coating for 10-200 s using the spin coating instrument to form the sacrificial layer, drying to obtain the tissue adhesive membrane.

5. The preparation method for the tissue adhesive membrane according to claim 4, wherein the thermal-initiated polymerization is performed at 50-100° C.; a mass fraction of the PVA aqueous solution is 5%-30%; and the spin coating is conducted at a speed of 500-5000 rpm and an acceleration of 50-1000 rpm.

6. The preparation method for the tissue adhesive membrane according to claim 4, wherein a thickness of the tissue adhesive membrane is not more than 2 mm.

\* \* \* \* \*